US009526783B1

(12) United States Patent
Das et al.

(10) Patent No.: US 9,526,783 B1
(45) Date of Patent: Dec. 27, 2016

(54) SPRAY COMPOSITION FOR TREATING AND PREVENTING DIAPER RASH

(71) Applicant: C. B. FLEET COMPANY INCORPORATED, Lynchburg, VA (US)

(72) Inventors: Debanjan Das, Lynchburg, VA (US); Ping Qiu, Roanoke, VA (US); Nelson P. Ayala, Lynchburg, VA (US)

(73) Assignee: C.B. Fleet Company Incorporated, Lynchburg, VA (US)

( * ) Notice: Subject to any disclaimer, the term of this patent is extended or adjusted under 35 U.S.C. 154(b) by 47 days.

(21) Appl. No.: 14/561,935

(22) Filed: Dec. 5, 2014

(51) Int. Cl.
    *A61K 47/02* (2006.01)
    *A61K 33/30* (2006.01)
    *A61K 47/44* (2006.01)
    *A61K 47/34* (2006.01)
    *A61K 9/00* (2006.01)
    *A61K 47/46* (2006.01)
    *A61K 47/14* (2006.01)

(52) U.S. Cl.
    CPC ............. *A61K 47/02* (2013.01); *A61K 9/0014* (2013.01); *A61K 33/30* (2013.01); *A61K 47/14* (2013.01); *A61K 47/34* (2013.01); *A61K 47/44* (2013.01); *A61K 47/46* (2013.01)

(58) Field of Classification Search
    None
    See application file for complete search history.

(56) References Cited

U.S. PATENT DOCUMENTS

| 5,869,033 | A | * | 2/1999 | Schulz | A61L 15/18 424/69 |
| 6,103,245 | A | | 8/2000 | Clark et al. | |
| 6,949,249 | B2 | | 9/2005 | Healy et al. | |
| 7,799,355 | B2 | * | 9/2010 | Avila | A61K 8/27 424/401 |
| 2005/0191257 | A1 | | 9/2005 | Brahms et al. | |
| 2005/0266035 | A1 | | 12/2005 | Healy et al. | |
| 2008/0145443 | A1 | | 6/2008 | Langolf et al. | |
| 2009/0317485 | A1 | | 12/2009 | Healy et al. | |
| 2009/0324506 | A1 | | 12/2009 | Seidling et al. | |
| 2012/0225106 | A1 | | 9/2012 | Ross et al. | |
| 2013/0058985 | A1 | | 3/2013 | Willems et al. | |

FOREIGN PATENT DOCUMENTS

| AU | 2011227841 | | 9/2011 | |
| WO | WO 0185128 A2 | * | 11/2001 | ............. A61K 8/046 |
| WO | 2016/090284 | | 6/2016 | |

OTHER PUBLICATIONS

The HLB system, a time-saving guide to emulsifier selection (ICI Americas, Mar. 1980).*
"Skin protectant active ingredients", Code of Federal Regulations, Title 21, Section 347.10 (Apr. 1, 2014).
(Continued)

*Primary Examiner* — Robert A Wax
*Assistant Examiner* — Melissa Mercier
(74) *Attorney, Agent, or Firm* — Evan Law Group LLC

(57) ABSTRACT

A composition for treating and preventing diaper rash comprises zinc oxide, dimethicone, mineral oil, a suspending agent, and an emulsifier. The emulsifier has a Hydrophile-Lipophile Balance number of at most 4.5 and the composition is sprayable. The suspending agent may be a hydrophobic clay.

24 Claims, 5 Drawing Sheets

LOG OF VISCOSITY VS LOG OF SPINDLE SPEED
ZnO COMPOSITION

(56) References Cited

OTHER PUBLICATIONS

"International Cosmetic Ingredient Dictionary and Handbook", The Cosmetic, Toiletry, and Fragrance Association, 12th edition, vol. 2, pp. 2136-2142, pp. 2620-2624, (2008).

"The HLB system a time-saving guide to emulsifier selection", ICI Americas Inc., pp. 1-22, Mar. 1980.

Product Information for "Original Boudreaux's Butt Paste®", pp. 1-2, found at www.buttpaste.com/products/original-butt-paste, Oct. 22, 2014.

"A Comparison of Smectite Clays in Underarm Products", Elementis Specialies, Inc., pp. 1-15, (2008).

Product Information for "Bentone Gel® Mio V HV". Elementis Specialties, Inc., pp. 1-2, Apr. 9, 2014.

"Veegum®/Van Gel® The Story", Vanderbilt Minerals, LLC, 11 pages, Oct. 15, 2014.

Product Information for "Hydrophobic fumed silica—Aerosil® fumed silica", pp. 1-2, found at www.aerosil.com/product/aerosil/en/products/hydrophobic-fumed-silica/Pages/default.aspx, Nov. 20, 2014.

Product Information for "Aerosil® R 972", Evonik Industries, AG, pp. 1-2, (Apr. 2014).

Product Information for "Kollicream® Grades Kollisolv® MCT Grades", BASF SE, pp. 1-8, Mar. 2012.

Definition of "Aerosol spray", pp. 1-5, found at en.wikipedia.org/wiki/Aerosol_spray, Oct. 1, 2014.

Definition of "Colloidal Silica", pp. 1-2, found at en.wikipedia.org/wiki/Colloidal_silica, Oct. 6, 2014.

Definition of "Curcumin", pp. 1-6, found at en.wikipedia.org/wiki/Curcumin, Oct. 20, 2014.

Definition of "Fumed Silica", pp. 1-3, found at en.wikipedia.org/wiki/Fumed_silica, Nov. 18, 2014.

Definition of "Rheopecty", pp. 1-2, found at en.wikipedia.org/wiki/Rheopecty, Jun. 9, 2014.

Definition of "Thixotropy", pp. 1-3, found at en.wikipedia.org/wiki/Thixotropy, Sep. 25, 2014.

Hwang, H.N. et al., "Preparation of silica-coated MWNTs and their addition to shear thickening fluid of silica/PEG suspension", 18th International Conference on Composite Materials, 4 pages, Aug. 23, 2011.

Bettin, G., "Energy absorption of reticulated foams filled with shear-thickening silica suspensions", M.S.E. dissertation, Massachusetts Institute of Technology, on file with Massachusetts Institute of Technology Libraries, pp. 1-98, Nov. 7, 2005.

Chafe, N.P. et al., "Drag and relaxation in a bentonite clay suspension", Journal of Non-Newtonian Fluid Mechanics, vol. 131, pp. 44-52, (2005).

Barnes, H.A., "Thixotropy—a review", Journal of Non-Newtonian Fluid Mechanics, vol. 70, pp. 1-33 (1997).

Galindo-Rosales, F.J. et al., "Structural breakdown and build-up in bentonite dispersions", Applied Clay Science, vol. 33, pp. 109-115, (2006).

Klepak, P. et al., "Antiperspirants and deodorants" Poucher's Perfumes, Cosmetics and Soaps, 10th Ed., pp. 69-100, (2000).

International Search Report dated May 4, 2016 for PCT application No. PCT/US2015/064061.

"Veegum®/Van Gel® The Products", Vanderbilt Minerals, LLC, 11 pages, Oct. 15, 2014.

Balch, P.A. "Prescription for herbal healing", Avery, pp. 23-24, 28-29, 40-41, 44-45, 48-49, 52-53, 64-65, 91-93, 259, (2002).

Calixto, J.B. et al., Anti-inflammatory compounds of plant origin. Part I. Action on arachidonic acid pathway, nitric oxide and nuclear factor KB (NF-KB), Planta Medica, vol. 69, No. 11, pp. 973-983, (2003).

Agnihotri, S. et al., "An overview on anti-inflammatory properties and chemo-profiles of plants used in traditional medicine", Indian Journal of Natural Products and Resources, vol. 1, No. 2, pp. 150-167, (2010).

Definition of "Balsam of Peru", pp. 1-6, found at en.wikipedia.org/wiki/Balsam_of_Peru, Jun. 23, 2016.

Product Information for "Maximum Stregth Boudreaux's Butt Paste®", pp. 1-2, found at www.buttpaste.com/products/high-strength-butt-paste, Oct. 21, 2014.

\* cited by examiner

SPRAY COMPOSITION FOR TREATING AND PREVENTING DIAPER RASH

BACKGROUND

Diaper rash is dermatitis or skin inflammation that occurs in the diaper area of young children. It is the most common dermatologic condition experienced during the first three years of life. Diaper rash most commonly occurs in babies 6-12 months of age.

The primary cause of diaper rash is prolonged or increased exposure to wetness to the skin, especially prolonged contact with urine or feces. Chafing due to friction against diapers or tight clothing may also lead to diaper rash. Diaper rash may be a result of dietary changes, such as when solid foods are introduced to the baby's diet. In breast-feeding mothers, certain foods that the mother consumes may lead to diaper rash in the baby. Diaper rash may also be caused by household products such as soaps, baby wipes, diapers, laundry detergents and fabric softeners. Infants with eczema and those receiving antibiotics are more prone to developing diaper rash.

Diaper rash may be treated and prevented with a topical skin protectant applied as a paste, ointment or cream. Skin protectants treat diaper rash by soothing the skin and prevent diaper rash by forming a barrier that seals out moisture. Skin protectants used in diaper rash compositions include organic compounds such as mineral oil, natural wax jelly, petrolatum and paraffin wax, and inorganic compounds such as dimethicone and zinc oxide.

Compositions for treating and preventing diaper rash are typically applied by hand. These compositions often have a greasy feel due to the presence of petroleum-based ingredients such as mineral oil or petrolatum. The compositions may be difficult to apply due to their high viscosity. Removing such compositions from the skin is particularly difficult due to both the high viscosity and the hydrophobic nature of the ingredients. These compositions may be very challenging to remove with soap and water, forcing users to either use stronger solvents or items such as cloths, paper towels or disposable wipes to remove them from the skin.

Compositions for treating and preventing diaper rash often require users to apply an indeterminate amount of product. For example, the instructions for BOUDREAUX'S BUTT PASTE® advise applying the product liberally in a thick, even layer. This product and similar compositions are generally packaged in jars, tubs, tins or squeezable tubes due to their viscous nature. It may be difficult to administer an appropriate dose of a composition for treating and preventing diaper rash from these types of containers. For example, a user who squeezes more ointment from a squeeze tube than is needed cannot return the excess ointment to the tube. Similarly, a user that applies a cream only to discover that more cream is needed may transfer cream from his or her hands to the product container when attempting to retrieve more cream. These application difficulties may lead to unintentional wasting of product.

SUMMARY

In a first aspect, the invention is a composition for treating and preventing diaper rash comprising zinc oxide, dimethicone, mineral oil, a suspending agent, and an emulsifier. The emulsifier has a Hydrophile-Lipophile Balance number of at most 4.5, and the composition is sprayable.

In a second aspect, the invention is a composition for treating and preventing diaper rash comprising 8.0% to 12.0% zinc oxide, 4.0% to 6.0% dimethicone, mineral oil, 5.0% to 16.0% hydrophobic clay, a phyto-extract, a first emulsifier, a second emulsifier, an antioxidant, a thickening agent, and an emollient. The emulsifier has a Hydrophile-Lipophile Balance number of at most 4.5, and the composition is sprayable.

In a third aspect, the invention is a composition for treating and preventing diaper rash comprising 9.0% to 11.0% zinc oxide, 4.5% to 5.5% dimethicone, mineral oil, a suspending agent, and an emulsifier. The emulsifier has a Hydrophile-Lipophile Balance number of at most 4.5, and the composition is sprayable. The composition is packaged in a container selected from the group consisting of spray pumps, aerosol spray containers, bag-on-valve containers and squeeze bottles.

DEFINITIONS

"Low shear" is measured by a viscometer spindle rotating at a speed of 0.6 revolutions per minute (RPM).

"High shear" is measured by a viscometer spindle rotating at a speed of 60 RPM.

A composition is "sprayable" if it has a viscosity of at most 400 centipoise at high shear.

A "phyto-extract" is a substance obtained from a plant. Preferably, the phyto-extract imparts a color. Phyto-extracts must be compatible with non-aqueous compositions; stable in air; non-staining to skin; non-irritating to skin exhibiting diaper rash in the amounts used; and non-toxic in the amounts used. The phyto-extract has a purity level of at least 95%. Examples of suitable phyto-extracts include curcumin, lycopene, beta-carotene, lutein, zeaxanthin, meso-zeaxanthin and anthocyanins. Sources of curcumin include turmeric. Sources of lycopene include beets, cherries, goji berries, pink grapefruit, pomegranate, raspberries, red cabbage, red onions, strawberries, tomatoes and watermelon. Sources of beta-carotene include apricots, cantaloupes, carrots, oranges, papayas, peaches, persimmons, pumpkins, summer squash, sweet potatoes, winter squash and yams. Sources of lutein, zeaxanthin, and meso-zeaxanthin include avocados, broccoli, Brussels sprouts, cabbage, green beans, leafy greens, orange peppers, peas, spinach, yellow corn and zucchini. Sources of anthocyanins include beets, black currants, blueberries, cherries, eggplant, figs, grapes, plums, prunes, red cabbage and red currants. Phyto-extracts may be chemically modified by hydrolysis, hydrogenation, esterification or saponification. Phyto-extracts which normally impart a color may no longer impart a color if they have been chemically modified. For example, curcumin imparts a yellow color but tetra-hydro curcumin, which has been hydrogenated, is colorless.

A "plant bio-extract" is a natural extract of a plant that provides a fragrance and may also provide a color. Plant bio-extracts must be compatible with non-aqueous compositions; stable in air; non-staining to skin; non-irritating to skin exhibiting diaper rash in the amounts used; and non-toxic in the amounts used. Synthetic versions of plant bio-extracts are outside the scope of the term "plant bio-extract." Examples of suitable plant bio-extracts include arnica extract (*Arnica montana*), basil extract (*Ocimum basilicum*), boswellia extract (*Boswellia sacra*), calendula extract (*Calendula officinalis*), chamomile extract (*Anthemis nobilis*), cinnamon oil (*Cinnamomum verum*), clove oil (*Syzygium aromaticum*), coptis extract (*Coptis aspleniifolia*), echinacea extract (*Echinacea purpurea*), eucalyptus oil (*Eucalyptus occidentalis*), ginger root extract (*Zingiber officinale*), grape seed extract (*Vitis vinefera*), green tea extract (*Camilia sinensis*), guggul resin extract (*Commiphora wightii*), horse chestnut seed extract (*Aesculus hippocastanum*), Japanese knotweed extract (*Polygonum cuspidatum*), licorice extract (*Glycyrrhiza glabra*), neem leaf extract (*Azadirachta indica*), olive fruit and olive leaf extract (*Olea europaea*), papaya extract (*Carica papaya*), Peruvian balsam (*Myroxylon balsamum*), pineapple extract (*Ananas comosus*), pomegranate extract (*Punica granatum* L.), rosemary extract (*Rosmarinus officinalis*), sage extract (*Salvia officinalis*), sandalwood extract (*Santalum album*), turmeric extract (*Curcuma longa*) and witch hazel extract (*Hamamelis japonica*). All the above examples may include different species of the same genus of plant. For example, witch hazel extract may be obtained from *Hamamelis japonica, Hamamelis ovalis, Hamamelis mollis* or *Hamamelis virginiana*.

A "low HLB emulsifier" has a Hydrophile-Lipophile Balance (HLB) number less than 7.0.

A "high HLB emulsifier" has an HLB number of 7.0 or greater.

"Controlled flocculation" is the formation of loose aggregates over time. In controlled flocculation the loose aggregates, or flocs, are easily returned to solution by mild agitation. Controlled flocculation does not result in the formation of a hard cake of insoluble aggregates by precipitation over time.

Viscosity is measured in centipoise (cps), unless stated otherwise.

All percentages (%) are weight/weight percentages, unless stated otherwise.

BRIEF DESCRIPTION OF THE DRAWINGS

The invention can be better understood with reference to the following drawings and description.

DETAILED DESCRIPTION

Figure 1:
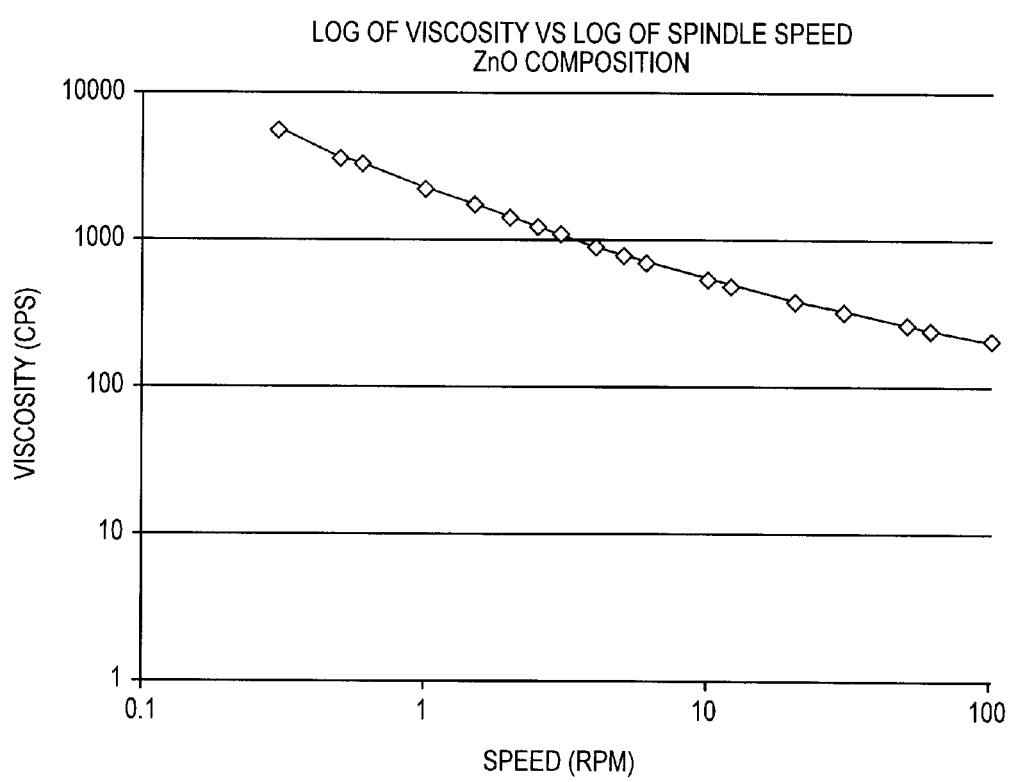
FIG. 1 is a graph of the log of viscosity versus the log of spindle speed for a spray composition for treating and preventing diaper rash.

The problems presented by applying and removing compositions for treating and preventing diaper rash may be solved by formulating a sprayable version of the composition. A sprayable composition for treating and preventing diaper rash could be administered by users without getting their hands messy. Also, spray dispensers deliver a predictable volume of product, which may prevent users from wasting excess product.

Products that will be sprayed onto the skin, such as compositions for treating and preventing diaper rash, must be able to be dispensed by spraying and still adhere to the skin after being sprayed. A sprayable composition that has weak adhesion to the skin may run off the skin after being sprayed and fail to provide the intended benefits. Sprayable products must also be able to withstand the shear forces introduced by spray administration, such as traveling up a siphon tube, passing through a nozzle or being atomized.

It is extremely challenging for manufacturers to balance the chemical and physical requirements of sprayable products. Various agents for adjusting rheological properties must not interfere with the active ingredients. Manufacturers must also package sprayable products in appropriate containers.

The present invention makes use of the discovery that hydrophobic clays may be used to suspend zinc oxide particles in mineral oil to form a non-aqueous composition for treating and preventing diaper rash with appropriate characteristics for application by spraying. The composition has good skin adherence and resists running after being sprayed onto skin. If aggregates form or if the ingredients settle, the composition may be easily returned to solution by mild shaking. The composition includes zinc oxide, dimethicone, mineral oil, a suspending agent and an emulsifier. The suspending agent may be a hydrophobic clay. The emulsifier has a Hydrophile-Lipophile Balance number of at most 4.5. The composition may optionally include a phytoextract, a plant bio-extract, an antioxidant, a thickening agent and/or an emollient. Preferably, the composition does not include a film-forming agent.

Applicants have also discovered that a non-aqueous composition for treating and preventing diaper rash preferably exhibits shear thinning to be sprayable while also demonstrating good skin adherence after being sprayed. Materials that demonstrate shear thinning experience a decrease in viscosity as shear forces increase. A spray composition for treating and preventing diaper rash will experience high shear during dispensing and low shear when on the skin. At low shear, the composition has a viscosity of at least 1,000 cps, preferably at least 10,000 cps. At high shear, the composition for treating and preventing diaper rash has a viscosity of at most 400 cps. Preferably, the viscosity range at high shear is 350-400 cps. Preferably, the composition has a minimum yield stress of 1.0 Pa or better.

In addition, applicants have discovered that a composition for treating and preventing diaper rash must be prepared according to a particular process to produce a sprayable composition. The ingredients cannot be simply added together and mixed. The ingredients must be added in a particular order and mixed at appropriate mixing speeds to produce a sprayable, homogeneous composition.

The composition for treating and preventing diaper rash includes zinc oxide as a skin protectant. Zinc oxide cools the skin and has antiseptic and antibacterial properties. The composition may contain 1.0% to 25.0% zinc oxide, preferably 5.0% to 15.0% zinc oxide, including 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0% and 14.5% zinc oxide. Preferably, the zinc oxide is U.S. Pharmacopeia (USP)-grade zinc oxide.

The composition includes dimethicone as a second skin protectant. Dimethicone forms a seal over the skin to prevent contact with potential irritants. The composition may contain 1.0% to 30.0% dimethicone, preferably 1.0% to 10.0% dimethicone, including 2.0%, 2.5%, 3.0%, 3.5%, 4.0%, 4.5%, 5.0%, 5.5%, 6.0%, 6.5%, 7.0%, 7.5%, 8.0%, 8.5%, 9.0% and 9.5% dimethicone. Dimethicone is a polymeric organosilicone compound and is available in multiple viscosities that are typically measured in centistokes. The dimethicone may have a viscosity from 5 centistokes to 500 centistokes, including 10 centistokes, 20 centistokes, 50 centistokes, 100 centistokes and 350 centistokes. Preferably, the dimethicone has a viscosity of 10-50 centistokes.

The composition includes mineral oil as a carrier. Mineral oil is a liquid mixture of hydrocarbons and is available in various forms. As the carrier, the amount of mineral oil may be varied to accommodate the other ingredients and ensure that the total amount of ingredients in the composition equals 100%. Preferably, the mineral oil is USP-grade white mineral oil 200.

The suspending agent may be a hydrophobic clay. Hydrophobic clays also prevent hard packing of suspended particles, making it easier to return the composition to dispersion with minimal agitation. The hydrophobic clay may be a smectite clay such as beidellite, bentonite, hectorite, nontronite, saponite, sauconite and sepiolite. A clay may be chemically or physically modified to increase its hydrophobic character. The composition may contain 1.0% to 20.0% hydrophobic clay, preferably 5.0% to 16.0%, including 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9% and 13.0% hydrophobic clay. A preferred hydrophobic clay is organically modified hectorite, such as BENTONE GEL® MIO V HV.

The composition optionally includes a phyto-extract. The phyto-extract may be selected to provide a color. Phyto-extracts that do not impart a color may also be included in the composition. Phyto-extracts must be compatible with non-aqueous compositions; stable in air; non-staining to skin; non-irritating to skin exhibiting diaper rash in the amounts used; and non-toxic in the amounts used. The phyto-extract has a purity level of at least 95%. Examples of suitable phyto-extracts include curcumin, lycopene, beta-carotene, lutein, zeaxanthin, meso-zeaxanthin and anthocyanins. Sources of curcumin include turmeric. Sources of lycopene include beets, cherries, goji berries, pink grapefruit, pomegranate, raspberries, red cabbage, red onions, strawberries, tomatoes and watermelon. Sources of beta-carotene include apricots, cantaloupes, carrots, oranges, papayas, peaches, persimmons, pumpkins, summer squash, sweet potatoes, winter squash and yams. Sources of lutein, zeaxanthin, and meso-zeaxanthin include avocados, broccoli, Brussels sprouts, cabbage, green beans, leafy greens, orange peppers, peas, spinach, yellow corn and zucchini. Sources of anthocyanins include beets, black currants, blueberries, cherries, eggplant, figs, grapes, plums, prunes, red cabbage and red currants. Phyto-extracts may be chemically modified by hydrolysis, hydrogenation, esterification or saponification. Phyto-extracts which normally impart a color, such as curcumin, may no longer impart a color if they have been chemically modified, such as tetra-hydro curcumin. The composition may contain 0.01% to 5.0% phyto-extract, preferably 0.01% to 1.0% phyto-extract, including 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19% and 0.20% phyto-extract.

The composition optionally includes a plant bio-extract. The plant bio-extract provides a fragrance and may also provide a color. Plant bio-extracts must be compatible with non-aqueous compositions, such as being lipophilic or hydrophobic; stable in air; non-staining to skin; non-irritating to skin exhibiting diaper rash in the amounts used; and non-toxic in the amounts used. Examples of suitable plant bio-extracts include arnica extract (*Arnica montana*), basil extract (*Ocimum basilicum*), boswellia extract (*Boswellia sacra*), calendula extract (*Calendula officinalis*), chamomile extract (*Anthemis nobilis*), cinnamon oil (*Cinnamomum verum*), clove oil (*Syzygium aromaticum*), coptis extract (*Coptis aspleniifolia*), echinacea extract (*Echinacea purpurea*), eucalyptus oil (*Eucalyptus occidentalis*), ginger root extract (*Zingiber officinale*), grape seed extract (*Vitis vinefera*), green tea extract (*Camilia sinensis*), guggul resin extract (*Commiphora wightii*), horse chestnut seed extract (*Aesculus hippocastanum*), Japanese knotweed extract (*Polygonum cuspidatum*), licorice extract (*Glycyrrhiza glabra*), neem leaf extract (*Azadirachta indica*), olive fruit and olive leaf extract (*Olea europaea*), papaya extract (*Carica papaya*), Peruvian balsam (*Myroxylon balsamum*), pineapple extract (*Ananas comosus*), pomegranate extract (*Punica granatum* L.), rosemary extract (*Rosmarinus officinalis*), sage extract (*Salvia officinalis*), sandalwood extract (*Santalum album*), turmeric extract (*Curcuma longa*) and witch hazel extract (*Hamamelis japonica*). The composition may contain 0.10% to 10.0% plant bio-extract, preferably 2.0% to 6.0% plant bio-extract, including 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9% and 4.0% plant bio-extract.

The composition includes an emulsifier to stabilize the ingredients and reduce separating. Preferably, the emulsifier is lipophilic in character, is oil-soluble and has a Hydrophile-Lipophile Balance (HLB) number of at most 4.5. If more than one emulsifier is used, the blend of emulsifiers preferably has an HLB number of at most 4.5. The composition may contain a single low HLB emulsifier, multiple low HLB emulsifiers, or a combination of low HLB emulsifiers and high HLB emulsifiers. Low HLB emulsifiers include sorbitan esters sold under the SPAN® trademark such as SPAN® 20 (sorbitan laurate), SPAN® 40 (sorbitan palmitate), SPAN® 60 (sorbitan stearate), SPAN® 65 (sorbitan tristearate), SPAN® 80 (sorbitan oleate) and SPAN® 85 (sorbitan trioleate). High HLB emulsifiers include polyethoxylated sorbitan esters sold under the TWEEN® trademark such as TWEEN® 20 (polysorbate 20), TWEEN® 21 (polysorbate 21), TWEEN® 40 (polysorbate 40), TWEEN® 60 (polysorbate 60), TWEEN® 65 (polysorbate 65), TWEEN® 80 (polysorbate 80) and TWEEN® 85 (polysorbate 85). The composition may contain 0.01% to 5.0% emulsifier, preferably 0.1% to 3.0% emulsifier, including 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0% emulsifier.

The composition optionally includes an oil-soluble antioxidant. When an antioxidant is present, the antioxidant is different than the phyto-extract. Examples of suitable antioxidants include carotene, catechin, lycopene, resveratrol, Vitamin E or Vitamin A. "Vitamin E" may refer to any of the tocopherol or tocotrienol compounds that constitute the Vitamin E family of compounds, such as alpha-tocopherol and gamma-tocotrienol. The composition may contain 0.01% to 5.0% antioxidant, preferably 0.1% to 3.0% antioxidant, including 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0% antioxidant.

The composition optionally includes a thickening agent. The thickening agent may reduce the rate of settling of ingredients in solution. The thickening agent may be silica, such as fumed silica or colloidal silica. Preferably, the silica is hydrophobic. Suitable thickening agents include hydrophobic silica products sold under the AEROSIL® trademark, such as AEROSIL® R 972, AEROSIL® R 972 Pharma, AEROSIL® R 974, AEROSIL® R 104, AEROSIL® R 106, AEROSIL® R 202, AEROSIL® R 208, AEROSIL® R 805, AEROSIL® R 812, AEROSIL® R 812S, AEROSIL® R 816, AEROSIL® R 7200, AEROSIL®

R 8200, AEROSIL® R 9200 and AEROSIL® R 711. The composition may contain 0.01% to 5.0% thickening agent, preferably 0.1% to 3.0% thickening agent, including 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0% thickening agent.

The composition optionally includes an emollient. The emollient may be a fatty acid ester such as alkyl esters or triglycerides. Preferably, the triglycerides are medium chain triglycerides. Suitable emollients include emollients sold under the KOLLICREAM® trademark, such as KOLLICREAM® 3C, KOLLICREAM® CI, KOLLICREAM® DO, KOLLICREAM® PH, KOLLICREAM® CP 15, KOLLICREAM® OD, KOLLICREAM® OA and KOLLICREAM® IPM. The composition may contain 0.01% to 5.0% emollient, preferably 0.1% to 3.0% emollient, including 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4% and 2.5% emollient.

The composition preferably does not contain water. Because the composition is non-aqueous, the inclusion of water might result in an immiscible aqueous layer. In addition, water could potentially ionize other elements of the composition, which could lead to the development of skin irritants. The composition may also exclude known skin irritants. For example, acids are often used to adjust pH or act as a preservative but may be painful to an infant with diaper rash.

The composition for treating and preventing diaper rash may include additional elements that do not materially affect the basic and novel characteristics of the composition. For example, the composition may optionally include fragrances, preservatives, colorants, dyes or stabilizers. Any additional elements must not impair the ability to apply the composition by spraying or alter the characteristics of the sprayed composition on the skin.

The composition for treating and preventing diaper rash may be packaged in a suitable container. Suitable containers include spray pumps, aerosol spray containers, bag-on-valve containers and squeeze bottles. The container may be pressurized or non-pressurized. If the container is pressurized, the pressure is preferably 40-60 pounds per square inch (psi).

The composition may experience controlled flocculation. Solutions which do not form flocs often develop hard cakes that cannot be returned to solution when components settle and agglomerate. Any flocs that form should be easily returned to solution with mild shaking. Preferably, the container, the product packaging and any included instructions will instruct users to shake the composition before use.

EXAMPLES

Example 1

A composition for treating and preventing diaper rash was prepared by mixing:
Zinc oxide—10.0%
Dimethicone 20 CST—5.0%
Mineral oil
A hydrophobic clay
A phyto-extract
A first low HLB emulsifier
A second low HLB emulsifier
An antioxidant Zinc oxide and dimethicone were included as skin protectants. Mineral oil was included as a carrier. The hydrophobic clay was included as a suspending agent. The emulsifier blend had a HLB value of 3.05, which indicated that it was lipophilic. Mixing the ingredients yielded a flocculated non-aqueous solution. The composition experienced controlled flocculation over time. The loose aggregates were easily returned to solution by mild shaking. The composition showed a shear thinning and thixotropic effect suitable for spray formulations and adhering to skin.

Example 2 (Comparative)

A composition for treating and preventing diaper rash was prepared by mixing:
Zinc oxide—10.0%
Dimethicone 20 CST—5.0%
Mineral oil
A hydrophobic clay
A phyto-extract
A first low HLB emulsifier
A second low HLB emulsifier
A first high HLB emulsifier
A second high HLB emulsifier
An antioxidant As compared to Example 1, this composition contained two additional high HLB emulsifiers. The emulsifier blend had a HLB value of 8.025, which indicated that it was less lipophilic than Example 1. The composition demonstrated superior suspension as compared to the composition of Exhibit 1 due to the inclusion of high HLB and low HLB emulsifiers. However, the clay could not be stabilized to form structure. The composition was not suitable for spray compositions.

Example 3 (Comparative)

A composition for treating and preventing diaper rash was prepared by mixing:
Zinc oxide—10.0%
Dimethicone 20 CST—5.0%
Mineral oil
A hydrophobic clay
A phyto-extract
A low HLB emulsifier
A high HLB emulsifier
An antioxidant As compared to Example 1, one of the low HLB emulsifiers was replaced with a high HLB emulsifier. The emulsifier blend had a HLB value of 9.65, which indicated that it was less lipophilic than Example 1. The composition demonstrated superior suspension due to the inclusion of high HLB and low HLB emulsifiers. However, the clay could not be stabilized, especially under stressed conditions, such as elevated temperatures. The composition was not suitable for spray compositions.

Example 4 (Comparative)

A composition for treating and preventing diaper rash was prepared by mixing:
Zinc oxide—10.0%
Dimethicone 20 CST—5.0%
Mineral oil
A hydrophilic clay
A phyto-extract
A low HLB emulsifier
An antioxidant As compared to Example 1, the hydrophobic clay was replaced with a hydrophilic clay as a suspending agent. Also, the composition contained a single low HLB emulsifier. The emulsifier had a HLB value of 1.8, which indicated that it was more lipophilic than Example 1. The composition was unstable and fell apart quickly (phase separated). The hydrophilic clay was not compatible with the mineral oil. The composition was not suitable for spray compositions.

Example 5 (Comparative)

A composition for treating and preventing diaper rash was prepared by mixing:
Zinc oxide—10.0%
Dimethicone 20 CST—5.0%
Mineral oil
Microcrystalline cellulose
A phyto-extract
A first low HLB emulsifier
A second low HLB emulsifier
An antioxidant As compared to Example 1, the hydrophobic clay was replaced with microcrystalline cellulose as a suspending agent. The emulsifier blend had a HLB value of 3.05, which indicated that it was as lipophilic as Example 1. The composition was unstable and fell apart quickly (phase separated). Microcrystalline cellulose was not compatible with the mineral oil. The composition was easy to apply and less greasy on the skin, but was not suitable for spray compositions.

Example 6 (Comparative)

A composition for treating and preventing diaper rash was prepared by mixing:
Zinc oxide—10.0%
Dimethicone 20 CST—5.0%
Mineral oil
A magnesium aluminum silicate clay
A phyto-extract
A first low HLB emulsifier
A second low HLB emulsifier
An antioxidant As compared to Example 1, the hydrophobic clay was replaced with a magnesium aluminum silicate clay as a suspending agent. The emulsifier blend had a HLB value of 3.05, which indicated that it was as lipophilic as Example 1. The composition was unstable and fell apart quickly (phase separated). The magnesium aluminum silicate clay was not compatible with the mineral oil. The composition was not suitable for spray compositions.

Example 7

A composition for treating and preventing diaper rash was prepared by mixing:
Zinc oxide—10.0%
Dimethicone 20 CST—5.0%
Mineral oil
A hydrophobic clay
A phyto-extract
A first low HLB emulsifier
A second low HLB emulsifier
An antioxidant
AEROSIL® R 972—1.50%
KOLLICREAM® 3C—1.0%

As compared to Example 1, this composition included AEROSIL® R 972, a thickening agent, and KOLLICREAM® 3C, an emollient. The emulsifier blend had a HLB value of 3.05, which indicated that it was as lipophilic as Example 1. The composition had significantly better physical properties than the composition of Example 1. The rate of settling was reduced and the thixotropic behavior was increased. This composition resisted running and demonstrated good adhesion properties.

Example 8

The composition of Example 1 was prepared according to the following process:
First, the phyto-extract was dissolved in the mineral oil under high shear. Next, the hydrophobic clay was added and the solution was mixed under moderate shear until it thickened. Then, the dimethicone, the antioxidant, the first low HLB emulsifier and the second low HLB emulsifier were added under stirring conditions. Finally, the zinc oxide was added stepwise under moderate shear. The solution was mixed until it appeared smooth and had a creamy texture.

Example 9

The composition of Example 7 was prepared according to the following process:
First, the phyto-extract, the first low HLB emulsifier and the second low HLB emulsifier were mixed with mineral oil under high shear mixing (3,000 RPM) for 15 minutes. Next, the zinc oxide was added under high shear mixing (3,000 RPM) for 15 minutes. Then, the AEROSIL® R 972 was added in small quantities under high shear mixing (3,000 RPM) for 15 minutes. Next, the dimethicone, the KOLLICREAM® 3C, and the antioxidant were added under moderate shear mixing (2,000 RPM) for 10 minutes. Finally, the hydrophobic clay was added under ultra low shear mixing (less than 500 RPM) with side sweeps and propeller mixing for 30 minutes. The temperature was maintained below 35° C. by cooling the system with a water jacket.

Example 10 (Comparative)

The composition of Example 7 was prepared according to the following process:
The zinc oxide, the dimethicone, the mineral oil, the hydrophobic clay, the phyto-extract, the first low HLB emulsifier, the second low HLB emulsifier, the antioxidant, the AEROSIL® R 972 and the KOLLICREAM® 3C were added simultaneously and mixed at high shear.

The resulting composition was heterogeneous and contained aggregates of varying sizes. The desired particle size distribution could not be achieved due to clumping of powdered ingredients. The composition was not suitable for spraying.

A comparison of Example 9 and Example 10 indicates that the specific order of adding the ingredients and the particular mixing conditions are vital to producing a composition for treating and preventing diaper rash that is sprayable.

Example 11

The effect of including a hydrophobic clay was demonstrated with an adherence test. Two compositions for treating and preventing diaper rash were prepared according to the process of Example 8. Composition A had the formulation listed in Example 1. Composition B had the same composition, except that the hydrophobic clay was excluded from the formulation.

1 gram of Composition A and 1 gram of Composition B were applied to a stainless steel platform. The platform was then moved to a vertical position and the time it took for each composition to travel 6 inches was measured. Composition A took 24 seconds to travel 6 inches. Composition B took 2 seconds to travel 6 inches. Thus, the adhesive properties of Composition A were 12 times better than the adhesive properties of Composition B. These results show that compositions for treating and preventing diaper rash that include a hydrophobic clay have superior adhesive properties as compared to compositions without a hydrophobic clay, even on a low-friction surface such as stainless steel.

Example 12

The effect of including a thickening agent and an emollient was demonstrated with an adherence test. Two compositions for treating and preventing diaper rash were prepared. Composition C had the formulation listed in Example 1. Composition D had the formulation listed in Example 7.

1 gram of Composition C and 1 gram of Composition D were applied to a stainless steel platform. The platform was then moved to a vertical position and the time it took for each composition to travel 6 inches was measured. Composition C took 24 seconds to travel 6 inches. Composition D took over 240 seconds to travel 6 inches. Thus, the adhesive properties of Composition D were more than 10 times better than the adhesive properties of Composition C. These results show that compositions for treating and preventing diaper rash that include a thickening agent and an emollient have superior adhesive properties as compared to compositions without a thickening agent and an emollient, even on a low-friction surface such as stainless steel.

Example 13

The viscosity of a composition for treating and preventing diaper rash with the formulation listed in Example 1 was measured with a BROOKFIELD® viscometer, spindle 62. The viscometer had a spindle speed range of 0.3-100 RPM. The viscosity was measured as the spindle speed was increased from 0.3 RPM to 100 RPM. The viscosity as measured at a given RPM is shown in the following table:

| RPM | Viscosity (centipoise) |
| --- | --- |
| 0.3 | 5599 |
| 0.5 | 3599 |
| 0.6 | 3249 |
| 1 | 2190 |
| 1.5 | 1720 |
| 2 | 1410 |
| 2.5 | 1212 |
| 3 | 1080 |
| 4 | 892 |
| 5 | 785.8 |
| 6 | 704.8 |
| 10 | 530.9 |
| 12 | 482.4 |
| 20 | 373.4 |
| 30 | 312.9 |
| 50 | 256.7 |
| 60 | 238.4 |
| 100 | 201 |

A graph of the log of viscosity versus the log of spindle speed is shown in FIG. 1.

As the spindle speed was increased, the viscosity of the composition decreased. These results indicate that the composition experienced shear thinning. The composition of Example 1 therefore demonstrated appropriate physical characteristics for application by spraying.

Example 14

The viscosities of two compositions for treating and preventing diaper rash were compared. One composition had the formulation of Example 1 while the second composition had the formulation of Example 7. The viscosity was measured with a BROOKFIELD® LV viscometer, spindle 62, at room temperature. The viscosity was measured as the spindle speed was increased from 0 to 100 RPM.

Figure 2:
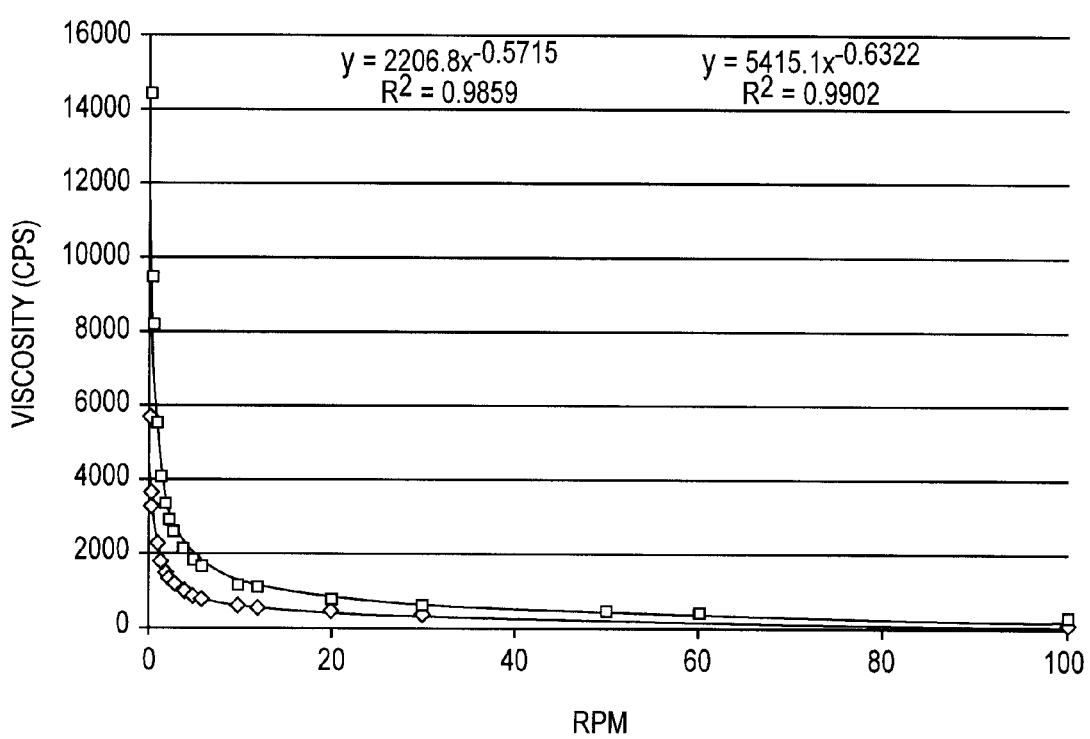
FIG. 2 is a graph of the viscosity versus the spindle speed for two spray compositions for treating and preventing diaper rash.

A graph of the viscosity versus the spindle speed for each composition is shown in FIG. 2. The diamond data points correspond to the composition of Example 1. The square data points correspond to the composition of Example 7. The viscosity of the composition of Example 1 at a given RPM fits the curve having the equation $y=2206.8x^{-0.5715}$. The coefficient of determination (also known as $R^2$) was 0.9859. The viscosity of the composition of Example 7 at a given RPM fits the curve having the equation $y=5415.1x^{-0.6322}$. The coefficient of determination was 0.9902.

As the spindle speed was increased, the viscosity of each composition decreased, indicating that both compositions experienced shear thinning and have appropriate physical characteristics for application by spraying. The viscosities were approximately equal at 30 RPM and greater. However, the composition of Example 7 demonstrated significantly greater viscosity below 30 RPM. The composition of Example 7 thus exhibited a preferred viscosity at both high shear and low shear.

Example 15

The viscoelasticities of two compositions for treating and preventing diaper rash were compared. One composition had the formulation of Example 1 while the second composition had the formulation of Example 7. The modulus of each composition was measured in an amplitude sweep experiment using a BOHLIN® CVO rheometer at controlled stress from 0.03 to 1.0 Pascals (Pa), 100 micron gap, 40 mm parallel plate at 25° C.

Figure 3:
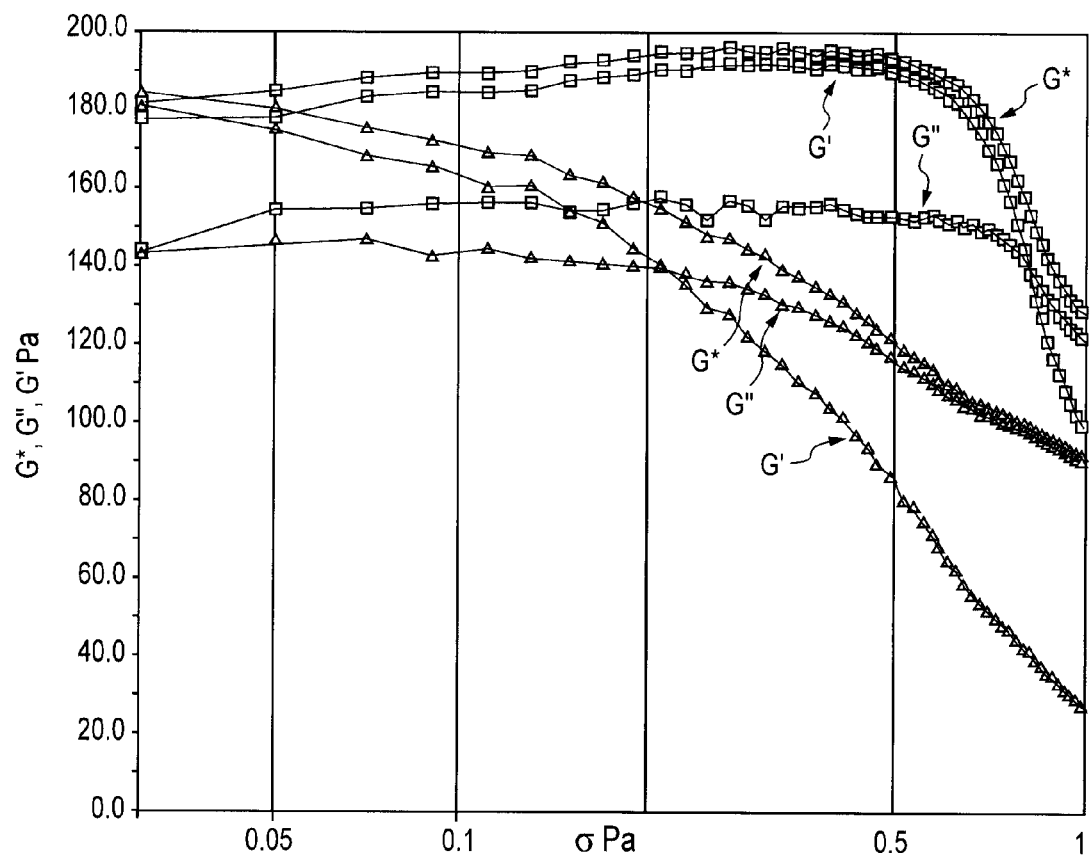
FIG. 3 is a graph of the modulus at the tangent of a given phase angle versus the controlled stress for two spray compositions for treating and preventing diaper rash.
Figure 5:
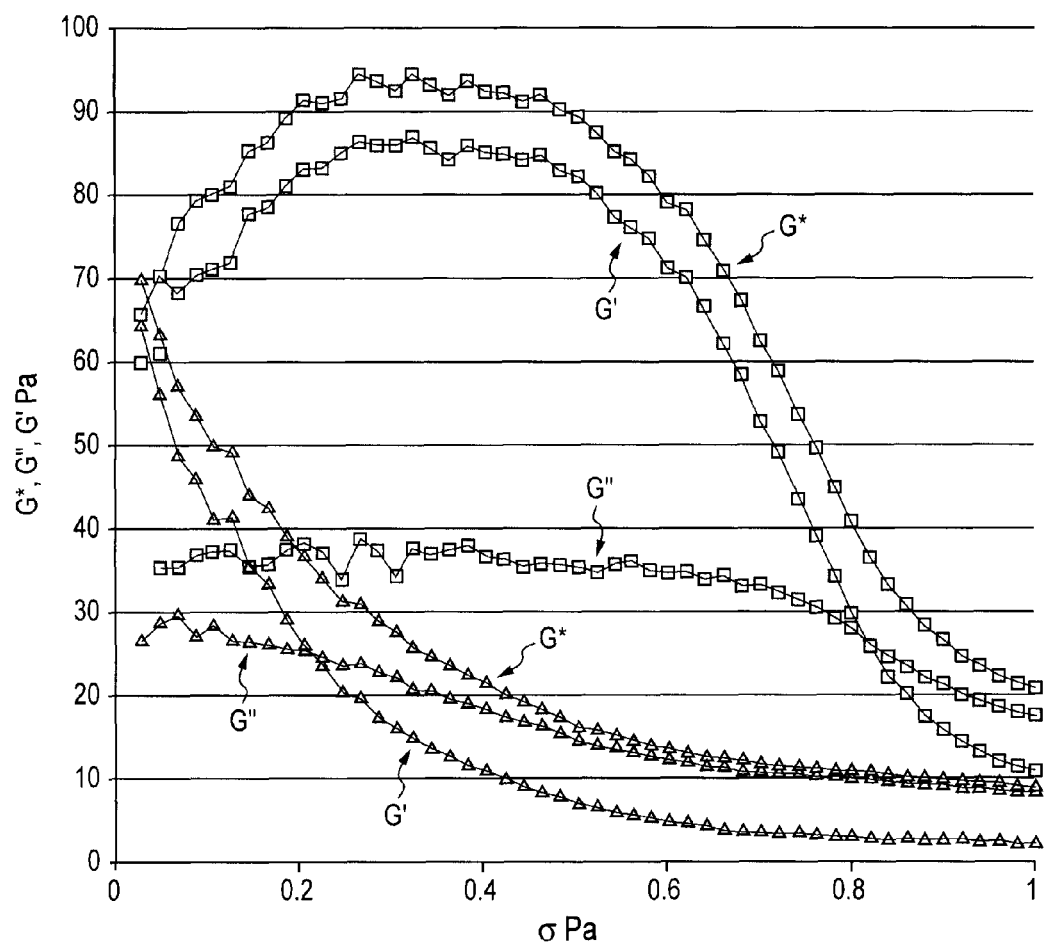
FIG. 5 is a graph of the modulus at the tangent of a given phase angle versus the controlled stress for two spray compositions for treating and preventing diaper rash.

A graph of the modulus at the tangent of a given phase angle versus the controlled stress for each composition is shown in FIG. 3 and in FIG. 5. The complex modulus (G*), elastic modulus (G') and the viscous modulus (G") were measured for each composition. The triangular data points correspond to the composition of Example 1. The square data points correspond to the composition of Example 7.

The composition of Example 7 exhibited a linear viscoelastic region from 0.03 to 0.7 Pa. The presence of a linear viscoelastic region is a sign of increased structure and improved suspension stability. The composition of Example 1 did not exhibit a linear viscoelastic region at any controlled stress. Thus, the composition of Example 7 demonstrated superior suspension as compared to the composition of Example 1.

Example 16

The yield stress and zero shear viscosity of a composition for treating and preventing diaper rash having the formulation of Example 7 were measured with a creep and creep recovery test. Creep and creep recovery were measured using a BOHLIN® CVO rheometer at constant applied stresses of 0.5 Pa, 0.7 Pa, and 1.0 Pa.

Figure 4:
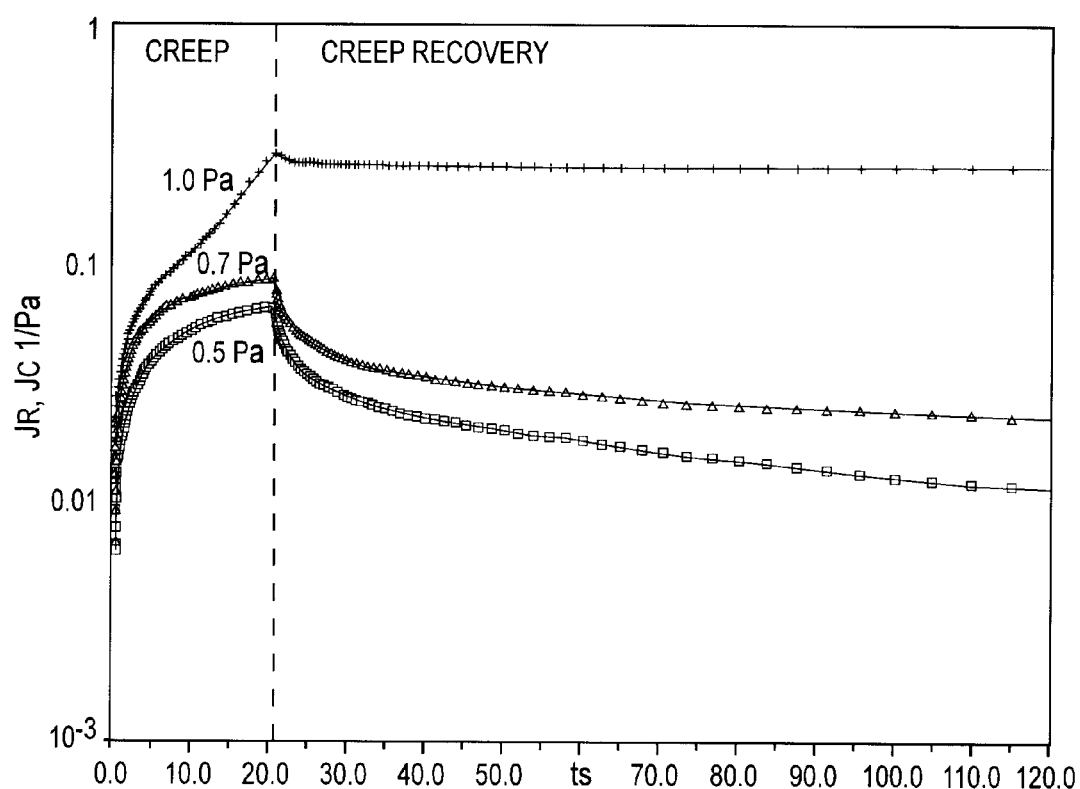
FIG. 4 is a graph of creep and creep recovery for a spray composition for treating and preventing diaper rash.

A graph of creep and creep recovery for each applied stress is shown in FIG. 4. Creep under applied stress was measured for 20.0 seconds. At 20.0 seconds the applied stress was removed and creep recovery was measured from 20.0 seconds to 115.0 seconds. The square data points correspond to the applied stress of 0.5 Pa. The triangular data points correspond to the applied stress of 0.7 Pa. The cross data points correspond to the applied stress of 1.0 Pa.

The curves for the applied stresses of 0.5 Pa and 0.7 Pa both exhibited a controlled recovery when the stress was removed. By contrast, the curve for the applied stress of 1.0 Pa exhibited a flat recovery when the stress was removed, signifying a broken structure. This indicated that the yield stress of the composition of Example 7 was 1.0 Pa. The data also showed that the zero shear viscosity of the composition of Example 1 was 51.5 Pa*s (equivalent to 51,500 cps), indicating an extremely high viscosity at rest.

REFERENCES

1. U.S. Pat. No. 6,103,245.
2. U.S. Pat. No. 6,949,249.
3. U.S. Pat. Pub. No. US2009/0317485.
4. U.S. Pat. Pub. No. US2013/0058985.
5. Australian Pat. App. No. AU 2011227841.
6. "Skin protectant active ingredients", Code of Federal Regulations, Title 21, Section 347.10 (Apr. 1, 2014).
7. "International and Cosmetic Ingredient Dictionary and Handbook", $12^{th}$ edition, Vol. (2), pp. 2136-2142, 2620-2624 (2008).
8. "HLB systems", available online at pharmcal.tripod.com/ch17.htm, accessed on Nov. 20, 2014.
9. "Original BOUDREAUX'S BUTT PASTE®", available online at www.buttpaste.com/products/original-butt-paste, accessed on Oct. 22, 2014.
10. "A Comparison of Smectite Clays in Underarm Products", Elementis Specialies, Inc. (2008).
11. "BENTONE GEL® MIO V HV", Elementis Specialties, Inc. (Apr. 9, 2014).
12. "VEEGUM®/VAN GEL® The Story", Vanderbilt Minerals, LLC (Oct. 15, 2014).
13. "Hydrophobic fumed silica—AEROSIL® fumed silica", available online at www.aerosil.com/product/aerosil/en/products/hydrophobic-fumed-silica/Pages/default.aspx, accessed on Nov. 20, 2014.
14. "AEROSIL® R 972", Evonik Industries, AG (April 2014).
15. "KOLLICREAM® Grades KOLLISOLV® MCT Grades", BASF SE (March 2012).
16. "Aerosol spray", available online at en.wikipedia.org/wiki/Aerosol_spray (Oct. 1, 2014).
17. "Colloidal Silica", available online at en.wikipedia.org/wiki/Colloidal_silica (Oct. 6, 2014).
18. "Curcumin", available online at en.wikipedia.org/wiki/Curcumin (Oct. 20, 2014).
19. "Fumed Silica", available online at en.wikipedia.org/wiki/Fumed_silica (Nov. 18, 2014).
20. "Rheopecty", available online at en.wikipedia.org/wiki/Rheopecty (Jun. 9, 2014).
21. "Thixotropy", available online at en.wikipedia.org/wiki/Thixotropy (Sep. 25, 2014).
22. Hwang, H. N. et al., "Preparation of silica-coated MWNTs and their addition to shear thickening fluid of silica/PEG suspension", $18^{th}$ International Conference on Composite Materials (Aug. 23, 2011).
23. Bettin, Giorgia, "Energy absorption of reticulated foams filled with shear-thickening silica suspensions", M.S.E. dissertation, Massachusetts Institute of Technology (on file with Massachusetts Institute of Technology Libraries, Nov. 7, 2005).
24. Chafe, N. P. et al., "Drag and relaxation in a bentonite clay suspension", Journal of Non-Newtonian Fluid Mechanics, vol. 131, pp. 44-52 (2005).
25. Barnes, H. A., "Thixotropy—a review", Journal of Non-Newtonian Fluid Mechanics, vol. 70, pp. 1-33 (1997).
26. Galindo-Rosales, F. J. et al., "Structural breakdown and build-up in bentonite dispersions", Applied Clay Science, vol. 33, pp. 109-115 (May 4, 2006).
27. Klepak, P. et al., "Antiperspirants and deodorants" in "Poucher's perfumes, cosmetics and soaps, $10^{th}$ Ed.", pp. 69-97 (Hilda Butler ed., Kluwer Academic Publishers, 2000).

What is claimed is:

1. A composition for treating and preventing diaper rash, comprising:
   zinc oxide,
   dimethicone,
   mineral oil,
   a suspending agent, and
   an emulsifier,
   wherein the emulsifier has a Hydrophile-Lipophile Balance number of at most 4.5, and
   the composition is sprayable.

2. The composition for treating and preventing diaper rash of claim 1, wherein the zinc oxide is present in an amount of 9.0% to 11.0%,
   the dimethicone is present in an amount of 4.5% to 5.5%, and
   the suspending agent is a hydrophobic clay.

3. The composition for treating and preventing diaper rash of claim 2, wherein the hydrophobic clay is a smectite clay selected from the group consisting of beidellite, bentonite, hectorite, nontronite, saponite, sauconite and sepiolite.

4. The composition for treating and preventing diaper rash of claim 3, wherein the smectite clay is hectorite.

5. The composition for treating and preventing diaper rash of claim 2, further comprising a phyto-extract,
   wherein the phyto-extract is selected from the group consisting of curcumin, lycopene, beta-carotene, lutein, zeaxanthin, meso-zeaxanthin, and anthocyanins.

6. The composition for treating and preventing diaper rash of claim 2, wherein the emulsifier is selected from the group consisting of sorbitan stearate, sorbitan tristearate, sorbitan oleate, and sorbitan trioleate; or
   the emulsifier is a combination of emulsifiers selected from the group consisting of sorbitan laurate, sorbitan palmitate, sorbitan stearate, sorbitan tristearate, sorbitan oleate, sorbitan trioleate, polysorbate 20, polysorbate 21, polysorbate 40, polysorbate 60, polysorbate 65, polysorbate 80, and polysorbate 85, such that the combination of emulsifiers has a Hydrophile-Lipophile Balance number of at most 4.5.

7. The composition for treating and preventing diaper rash of claim 2, further comprising an antioxidant,
   wherein the antioxidant is selected from the group consisting of carotene, catechin, lycopene, resveratrol, Vitamin E, and Vitamin A.

8. The composition for treating and preventing diaper rash of claim 2, further comprising a thickening agent,
   wherein the thickening agent is hydrophobic silica.

9. The composition for treating and preventing diaper rash of claim 2, further comprising an emollient,
wherein the emollient is a fatty acid ester selected from the group consisting of alkyl esters and triglycerides.

10. The composition for treating and preventing diaper rash of claim 2, further comprising a plant bio-extract.

11. The composition for treating and preventing diaper rash of claim 2, wherein the composition does not contain water.

12. The composition for treating and preventing diaper rash of claim 2, wherein 1 gram of the composition travels 6 inches on a stainless steel surface in greater than 20 seconds after being sprayed onto the surface.

13. The composition for treating and preventing diaper rash of claim 2, wherein 1 gram of the composition travels 6 inches on a stainless steel surface in greater than 200 seconds after being sprayed onto the surface.

14. The composition for treating and preventing diaper rash of claim 2, wherein the composition demonstrates shear thinning.

15. The composition for treating and preventing diaper rash of claim 2, wherein the composition has a viscosity of 350-400 centipoise at high shear.

16. A composition for treating and preventing diaper rash, comprising:
    8.0% to 12.0% zinc oxide,
    4.0% to 6.0% dimethicone,
    mineral oil,
    5.0% to 16.0% hydrophobic clay,
    a phyto-extract,
    a first emulsifier,
    a second emulsifier,
    an antioxidant,
    a thickening agent, and
    an emollient,
    wherein the first emulsifier and the second emulsifier together have a Hydrophile-Lipophile Balance number of at most 4.5, and
    the composition is sprayable.

17. The composition for treating and preventing diaper rash of claim 16, wherein the phyto-extract is present in an amount of 0.01% to 0.15%,
    the first emulsifier is present in an amount of 0.4% to 0.6%,
    the second emulsifier is present in an amount of 0.4% to 0.6%,
    the antioxidant is present in an amount of 0.4% to 0.6%,
    the thickening agent is present in an amount of 0.1% to 3.0%, and
    the emollient is present in an amount of 0.1% to 3.0%.

18. A method of making the composition for treating and preventing diaper rash of claim 16, comprising:
    mixing first ingredients comprising the phyto-extract, the first emulsifier, and the second emulsifier with mineral oil to form a first intermediary;
    mixing second ingredients comprising the zinc oxide with the first intermediary to form a second intermediary;
    mixing third ingredients comprising the thickening agent with the second intermediary to form a third intermediary;
    mixing fourth ingredients comprising the dimethicone, the emollient, and the antioxidant with the third intermediary to form a fourth intermediary; and
    mixing fifth ingredients comprising the hydrophobic clay with the fourth intermediary to form the composition for treating and preventing diaper rash;
    wherein the temperature of the intermediaries and the composition is maintained below 35° C.

19. A method of treating and preventing diaper rash, comprising:
    applying the composition of claim 1 to skin.

20. A composition for treating and preventing diaper rash, comprising:
    9.0% to 11.0% zinc oxide,
    4.5% to 5.5% dimethicone,
    mineral oil,
    a suspending agent, and
    an emulsifier,
    wherein the emulsifier has a Hydrophile-Lipophile Balance number of at most 4.5,
    the composition is sprayable, and
    the composition is packaged in a container selected from the group consisting of spray pumps, aerosol spray containers, bag-on-valve containers and squeeze bottles.

21. The composition for treating and preventing diaper rash of claim 1, wherein the first emulsifier has a Hydrophile-Lipophile Balance number less than 7.0,
    the second emulsifier has a Hydrophile-Lipophile Balance number less than 7.0,
    the thickening agent is present in an amount of 0.1% to 3.0%,
    the emollient is present in an amount of 0.1% to 3.0%, and
    the first emulsifier and the second emulsifier together have a Hydrophile-Lipophile Balance number between 2.0-4.0.

22. The composition for treating and preventing diaper rash of claim 1, wherein the emulsifier has a Hydrophile-Lipophile Balance number between 2.0-4.0.

23. The composition for treating and preventing diaper rash of claim 16, further comprising a plant bio-extract.

24. The composition for treating and preventing diaper rash of claim 20, further comprising a plant bio-extract.

* * * * *